(12) United States Patent
Ritt et al.

(10) Patent No.: US 7,977,109 B2
(45) Date of Patent: Jul. 12, 2011

(54) METHOD FOR ENRICHING SHORT-CHAIN NUCLEIC ACIDS

(75) Inventors: Christoph Ritt, Lagenfeld (DE); Ralf Himmelreich, Langenfeld (DE); Martin Weber, Leichlingen (DE)

(73) Assignee: Qiagen GmbH, Hilden (DE)

( * ) Notice: Subject to any disclaimer, the term of this patent is extended or adjusted under 35 U.S.C. 154(b) by 119 days.

(21) Appl. No.: 12/096,155

(22) PCT Filed: Dec. 8, 2006

(86) PCT No.: PCT/EP2006/069484
§ 371 (c)(1),
(2), (4) Date: Oct. 28, 2008

(87) PCT Pub. No.: WO2007/065950
PCT Pub. Date: Jun. 14, 2007

(65) Prior Publication Data
US 2009/0081802 A1 Mar. 26, 2009

(30) Foreign Application Priority Data

Dec. 9, 2005 (DE) .......................... 10 2005 059 315

(51) Int. Cl.
*G01N 30/00* (2006.01)
(52) U.S. Cl. ............. 436/94; 436/63; 436/161; 436/178
(58) Field of Classification Search .................. None
See application file for complete search history.

(56) References Cited

U.S. PATENT DOCUMENTS

| 5,523,231 A * | 6/1996 | Reeve ........................... 435/270 |
| 5,990,301 A | 11/1999 | Colpan et al. |
| 6,037,465 A * | 3/2000 | Hillebrand et al. ........ 536/25.42 |
| 6,284,470 B1 | 9/2001 | Bitner et al. |
| 6,410,274 B1 * | 6/2002 | Bhikhabhai .................. 435/91.1 |
| 2005/0079535 A1 | 4/2005 | Kirchgesser et al. |
| 2007/0172855 A1 * | 7/2007 | Bitner et al. ...................... 435/6 |
| 2010/0256351 A1 * | 10/2010 | Chen et al. ................... 536/25.4 |

FOREIGN PATENT DOCUMENTS

| WO | WO 83/03920 A1 | 11/1983 |
| WO | WO 03/080834 A2 | 10/2003 |

OTHER PUBLICATIONS

McNeff, Clatyton et al. "High-performance anion-exchange chromatography of oligonucleotides and oligodeoxynucleotides on quaternized polyethylenimine-coated zirconia." Analytical Chemistry (1995) 67 p. 2350-2353.*
Eon-Duval, Alex et al. "Precipitation of RNA impurities with high salt in a plasmid DNA purification process: use of experimental design to determine reaction conditions." Biotechnology and Bioengineering (2003) 83 544-553.*
Yang, Yu et al. "High performance DNA purification using a novel ion exchange matrix." Journal of Biomolecular Techniques (2008) 19 205-210.*
International Search Report for PCT/EP2006/069484, dated Apr. 19, 2007, English and German Form PCT/ISA1210—(7 pages).
Guenther, R. H. et al., "Purification of transfer RNA species by single-step ion-exchange high-performance liquid chromatorgraphy"; Journal of Chromatography, pp. 79-87, vol. 444, Jul. 1, 1988, XP0092447076, ISSN: 0021-9673.
Drager, R. R. et al., "High-performance anion-exchange chromatography of oligonucleotides"; Analytical Biochemistry, 1985, United States, pp. 47-56, vol. 145, No. 1, 1985, XP009080610.
Lawson, T. G. et al., "Separation of synthetic oligonucleotides on columns of microparticulate silica coated with crosslinked polyethylene imine", Analytical Biochemistry, pp. 85-93, vol. 133, No. 1, Aug. 1983, XP009080633, ISSN: 0003-2697.
Chaing, C. L. et al., "Application of superparamagnetic nanoparticles in purification of plasmid DNA from bacterial cells"; Journal of Chromatography B; Biomedical Sciences & Applications, pp. 54-60, vol. 822, No. 1-2, Aug. 5, 2005, Elsevier, Amsterdam, NL, XP004987301l, USSN: 1570-0232.
Sambrook, J. et al., "Isolation of High-molecular-weight DNA from Mammalian Cells", pp. 9.14-9.19, Analysis and Cloning of Eukaryotic Genomic DNA, Molecular Cloning, A Laboratory Manual, second edition, 1989, Cold Spring Harbor Laboratory Press.

* cited by examiner

*Primary Examiner* — Yelena G Gakh
*Assistant Examiner* — Christopher A Hixson
(74) *Attorney, Agent, or Firm* — Baker Donelson, Bearman Caldwell & Berkowitz

(57) ABSTRACT

The present invention relates to a method for enriching nucleic acids with a length of not more than 300 nucleotides. The invention also relates to a kit for enriching nucleic acids with a length of not more than 300 nucleotides, to the use of such a kit, to the use of an anion exchange matrix and to a method for treating a disease.

17 Claims, 5 Drawing Sheets

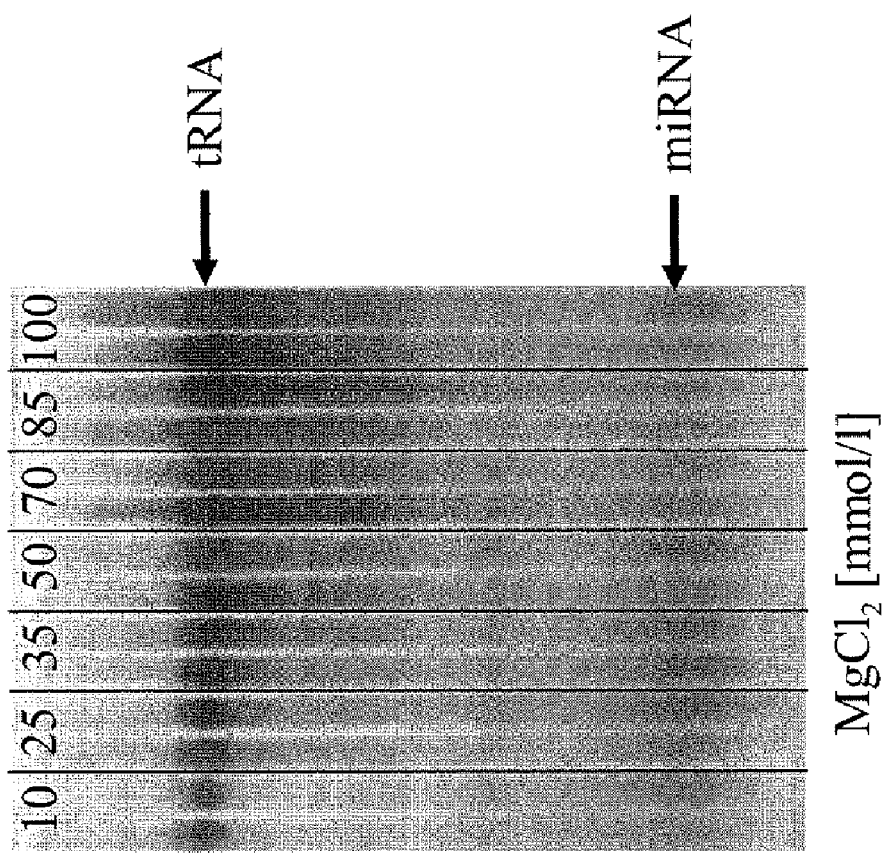

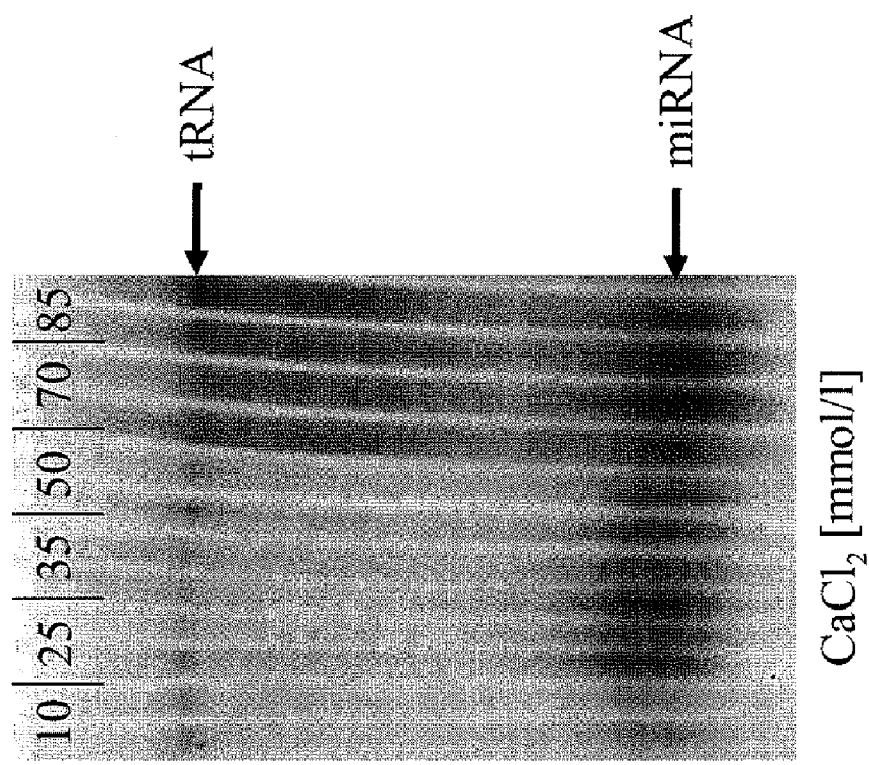

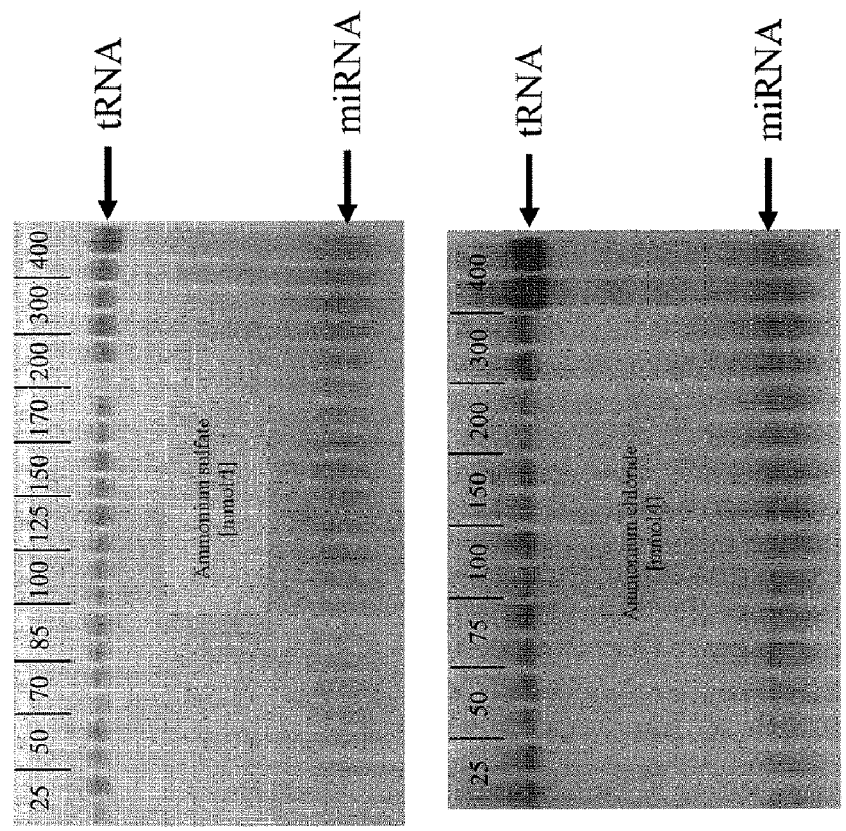

METHOD FOR ENRICHING SHORT-CHAIN NUCLEIC ACIDS

CROSS REFERENCE TO RELATED APPLICATIONS

This application is a §371 National Stage Application of PCT/EP2006/069484, filed Dec. 8 2006, which claims priority from German Application 10 2005 059 315.1, filed Dec. 9, 2005.

BACKGROUND OF THE INVENTION

1. Field of the Invention

The present invention relates to a method for enriching nucleic acids with a length of less than 300 nucleotides, to a kit for enriching nucleic acids with a length of less than 300 nucleotides, to the use of said kit, to the use of an anion exchange matrix and to a method for treating a disease.

2. Description of Related Art

Since small ribonucleic acids (RNAs) were found, a few years ago, to carry out an essential regulatory function in gene expression, scientific studies have increasingly concentrated on small RNAs shorter than 300 nucleotides, in particular shorter than 100 nucleotides. More specifically, many researchers have become interested in micro RNAs (miRNAs). miRNAs are an evolutionarily conserved class of small noncoding RNAs of about 22 nucleotides in length, whose complex role during regulation of gene expression is becoming more and more obvious. miRNAs have been found in any eukaryotic organism studied and in nearly every tissue, inter alia in fungi, plants, insects and mammals. Aside from miRNAs, other small RNAs have also been found which likewise play a fundamental role in cellular functions. These include, for example, small interfering RNAs (siRNAs), small nuclear RNAs (snRNAs) and small nucleolar RNAs (snoRNAs).

These short RNAs which are shorter than 300 nucleotides must be as pure as possible and purified with high yield from the biological systems to be studied in order for it to be possible for their cellular role to be investigated. There is therefore a great need to provide a method which enables such short RNAs to be purified or isolated from complex biological systems, in particular from cell lysates.

Generally, in order to isolate nucleic acids from biological samples, they must be separated from the remaining cellular components such as proteins, sugars, lipids and other components. The prior art has disclosed a plurality of methods of separating nucleic acids from very different starting materials, for example from cell cultures, from tissues of plant and animal origin and from body fluids. One method, for example, includes extracting the usually aqueous starting solutions with the aid of organic solvents such as phenol and chloroform (Chomczynski and Sacchi, 1987) followed by precipitation of the nucleic acids with the aid of alcohols such as ethanol or isopropanol from the aqueous phase (Sambrook, J., Fritsch, E. F. in T. Maniatis, CSH, *"Molecular Cloning"*, 1989). Another method comprises immobilizing the nucleic acids to a solid phase, for example by means of silica adsorption technology. Disadvantageously, it is not, or only insufficiently, possible in all of these methods to isolate or at least purify relatively small nucleic acids.

To solve this problem, the prior art has disclosed methods for specifically enriching small RNA populations, which methods are based on silica membrane technology. In these methods, a specific, relatively small amount of alcohol is added to the cell lysate after the cells have been lysed, and at least part of the relatively long nucleic acids are bound to the silica membrane under chaotropic binding conditions. However, the amount of alcohol in the purification methods described in the prior art is too low to bind efficiently also small nucleic acids to the silica membrane, and these small RNAs are therefore present in the breakthrough. The alcohol concentration is then increased in the breakthrough and the latter is bound to a second silica membrane. After washing steps, the small RNA is eluted together with all other nucleic acids that have not been bound to the first column (see, for example, mirVana® kit from Ambion, Austin, USA or RNeasy® Lipid Tissue Mini Kit from QIAGEN, Hilden, Germany, to be used by means of the "user developed protocols").

The disadvantage of both the QIAGEN and the Ambion methods is that of two solid phases having to be used and it not being possible to obtain only the desired small RNA with the aid of a single binding step. Moreover, this method does not enable, for example, only miRNAs of about 22 nucleotides in size to be isolated, without isolating also tRNAs and other larger nucleic acids at the same time. Although it is possible to enrich the small RNA, in particular the miRNA, to a certain degree by this method under some circumstances, said small RNA is still contaminated with other nucleic acids, in particular with transfer RNA (tRNA).

SUMMARY OF THE INVENTION

The object of the present invention was that of overcoming the disadvantages arising from the prior art.

More specifically, it was the object of the present invention to provide a method for enriching small nucleic acids, in particular miRNA, which method enables small nucleic acids to be enriched from complex biological compositions, such as cell lysates for example, using as few method steps as possible.

It was also an object of the present invention to provide a method for purifying small nucleic acids, which not only enables in particular nucleic acids with a length of 25 nucleotides or less, for example miRNAs, to be removed from nucleic acids with a length of more than 300 nucleotides of other components in a complex biological composition such as a cell lysate, for example, but also enables these small nucleic acids to be specifically removed from other nucleic acids with a length of less than 300 and more than 25 nucleotides, for example tRNAs.

It was also intended to provide a method which can be used to generate, as individually as possible, a desired size exclusion for the RNA to be purified.

It is also the object of the present invention to provide a method which can be carried out without changing the reaction vessel—by way of a "one-pot reaction"—, thereby reducing to a minimum the risk of mixing up the samples to be analyzed.

It was furthermore the object of the invention to provide a kit with the aid of which it is possible to carry out the above-described, advantageous purification of small nucleic acids, in particular of small RNA, from complex biological compositions.

A contribution to the solution of the objects mentioned above is made by a method for enriching nucleic acids with a length of less than 300 nucleotides, preferably less than 200 nucleotides, particularly preferably less than 100 nucleotides, additionally preferably less than 50 nucleotides, and most preferably less than 25 nucleotides, comprising the method steps of i) providing a fluid, preferably aqueous, phase $P_1$ containing
  (α1) at least one nucleic acid with a length of less than 300 nucleotides, preferably less than 200 nucleotides, particularly preferably less than 100 nucleotides, additionally preferably less than 50 nucleotides and most preferably less than 25 nucleotides, and ($\alpha$2) at least one component different from said nucleic acid ($\alpha$1), ii) contacting the phase $P_1$ with an anion exchange matrix to bind the nucleic acid ($\alpha$1) to the anion exchange matrix, iii) optionally washing the anion exchange matrix with a washing buffer, wherein the nucleic acid ($\alpha$1) remains bound to the anion exchange matrix, and iv) removing, preferably eluting, the nucleic acid ($\alpha$1) bound to the anion exchange matrix from said anion exchange matrix to obtain a fluid, preferably aqueous, phase $P_2$ containing the nucleic acid ($\alpha$1).

Very surprisingly, it was found that small nucleic acids with a length of less than 300 nucleotides can be enriched from complex biological compositions which may contain numerous other components in addition to said small nucleic acids, by binding to an anion exchange matrix and subsequent washing and eluting, without the need for firstly diluting longer nucleic acids, as is required in the QIAGEN and Ambion methods described above.

DETAILED DESCRIPTION OF A PREFERRED EMBODIMENT

According to a preferred embodiment of the method of the invention, the nucleic acid ($\alpha$1) to be purified is a single-stranded or double-stranded, preferably double-stranded, RNA. More specifically, preference is given to the RNA with a length of less than 300 nucleotides being an RNA selected from the group comprising miRNA, pre-miRNA, siRNA, snRNA, snoRNA, tRNA, 5S-rRNA, 5.8S-rRNA or mixtures of at least two therefrom, in particular a mixture of miRNA and tRNA, most preference being given to the nucleic acid ($\alpha$1) being miRNA with a length within a range from 15 to 30 nucleotides, additionally preferably 17 to 24 nucleotides and even more preferably with a length of from 20 to 23 nucleotides.

The terms "5S-rRNA" and "5.8S-rRNA" mean noncoding ribonucleic acids which can be found in eukaryotic ribosomes. The term "tRNA" means a ribonucleic acid consisting of about 80 nucleotides and containing pairings of conjugating bases (adenine and uracil; cytosine and guanine). These pairings cause the cloverleaf-like structure of tRNA. The term "siRNA" means ribonucleic acids with a length of about 22 nucleotides, which are produced by way of cleavage of a double-stranded RNA (dsRNA) by the enzyme "dicer" and incorporated into the "RISC" (RNA-induced silencing complex) enzyme complex. The term "snRNA" means catalytically active RNAs of about 100 to 300 base pairs in size in the nucleus of eukaryotes. These snRNAs are always associated with proteins in "snRNPs" (small nuclear ribonucleoproteins) and are responsible for splicing the introns out of pre-mRNA to give mRNA. The term "snoRNA" means a class of ribonucleic acids which are involved in chemical modification of ribosomal RNA (rRNA) and other RNA genes, for example in methylation thereof. They form one part of the "snoRNPs" (small nucleolar ribonucleoproteins). The term "miRNA" means small nucleic acids which are used for regulating developmental processes in plants and animals. They bind specifically to mRNA and prevent the activity of the latter in translation, preventing for example growth factors from being produced in excess. miRNAs are single-stranded RNA molecules produced from a double-stranded precursor.

The component ($\alpha$2) different from the nucleic acids with a length of no more than 300 nucleotides ($\alpha$1) is in particular nucleic acids with a length of at least 300 nucleotides ($\alpha$2') and components ($\alpha$2") different from nucleic acids.

Nucleic acids with a length of at least 300 nucleotides ($\alpha$2') comprise in particular single-stranded or double-stranded DNA molecules or single-stranded or double-stranded RNA molecules, for example mRNA, 18S-rRNA or 28S-rRNA.

Components ($\alpha$2") different from the nucleic acids are in particular those components which are released during lysis of a cell. Accordingly, these components include in particular proteins, lipids, polypeptides or polysaccharides.

The fluid, preferably aqueous, phase $P_1$ provided in the method step i) may be a cell-free sample material, a plasma, a serum, a bodily fluid such as, for example, blood, urine, sperm, saliva, cerebrospinal fluid, sputum or a surface biopsy, waste water, sludge or else a cell lysate, for example a lysate of cells from animal or plant tissues, from microorganisms such as bacteria, fungi or yeasts, from tissue cultures or cell cultures, or else of cells from bodily fluids such as blood.

According to a particular embodiment of the method of the invention, the fluid, preferably aqueous, phase $P_1$ provided in the method step i) is a cell lysate obtainable by a method comprising the method steps of I) providing cells, II) lyses of the cells to obtain a cell lysate, and III) optionally separating at least partially the at least one component ($\alpha_2$) different from the nucleic acid ($\alpha_1$) from the cell lysate.

The cells which are provided in the method step I) may be an optionally fixed tissue section or an optionally fixed tissue fragment, cultured, adherent cells, cultured cells in suspension or else a cell in a bodily fluid.

If the cells are adherent cells or cells within a tissue assemblage, the method step I) may optionally comprise washing the adhered cells or the tissue, detaching the adhered cells or removing the cells from the tissue assemblage using suitable enzyme solutions, solutions containing complexing compounds such as EDTA, for example, or mixtures thereof, optionally separating particular cell populations from the cell suspensions thus obtained, for example by means of a cell sorter, pelleting the detached or separated cells, washing the cell pellet thus obtained and optionally resuspending in a suitable suspension buffer. However, it is also conceivable to lyse the adherent cells without prior detachment, where appropriate after a washing step.

If the cells are cultured cells in suspension or cells in a bodily fluid, the method step I) preferably comprises pelleting the suspended cells, where appropriate after removing particular cell populations, for example by means of a cell sorter, washing the cell pellet thus obtained and optionally resuspending in a suitable suspension buffer.

The suspension buffer in which the pelleted cells are optionally resuspended preferably contains one or more buffer substances and optionally one or more complexing compounds. The pH of the suspension buffer may be varied over a wide range and is, for carrying out the method of the invention, preferably within a range from pH 3 to 11, additionally preferably in a range from 5 to 10, and most preferably in a range from pH 7 to 9. The buffer systems known to the skilled worker for adjusting the pH may be used here. Preference is given according to the invention to using buffer systems based on tris(hydroxymethyl)aminomethane (TRIS), morpholinopropanesulfonic acid (MOPS), or 2-[4-(2-hydroxyethyl)-1-piperazino]ethanesulfonic acid (HEPES), which include the buffer component at a concentration in a range from 0.5 to 100 mmol/l, additionally preferably in a range from 1 to 50 mmol/l and most preferably in a range from 2.5 to 25 mmol/l. Buffer systems based on alkali metal acetate/acetic acid or mixtures of an alkali metal acetate/acetic acid buffer system and a tris(hydroxymethyl) aminomethane buffer system are also conceivable. Complexing compounds which may be used are likewise any compounds capable of complexing specifically calcium ions. A preferred complexing compound is ethylenediaminetetraacetate (EDTA) which is present in the suspension buffer preferably in an amount in a range from 0.01 to 20 mmol/l, additionally preferably 0.1 to 15 mmol/l and most preferably 0.5 to 5 mmol/l.

The amount of suspension buffer to be used depends on the number of cells provided. Usually, an amount of suspension buffer in a range from 10 to 2000 μl, particularly preferably 50 to 1000 μl and most preferably 100 to 500 μl, per $10^6$ cells is used.

A suspension buffer which is particularly suitable according to the invention is a buffer which contains from 0.5 to 100 mmol/l, particularly preferably 1 to 50 mmol/l and most preferably about 2.5 to 25 mmol/l, tris(hydroxymethyl)aminomethane and from 0.01 to 20 mmol/l, particularly preferably 0.1 to 15 mmol/l and most preferably 0.5 to 5 mmol/l, EDTA and which has a pH in a range from 7 to 9, particularly preferably of about 8.

In the method step II), the cells provided are lysed, it being possible to employ for lysis of the cells any lysis methods known to the skilled worker which are suitable for releasing specifically RNA material from cells. Lysis methods which may be contemplated are in particular lysis by the action of heat, lysis by the action of mechanical force, lysis by enzymes such as, for example, protein kinase K, or lysis by contacting the cells to a lysis buffer containing a detergent or a chaotropic compound, or by means of hypotonic solutions. Where appropriate, the abovementioned measures may also be combined, for example by mechanically disrupting the cells in a lysis buffer containing a detergent or a chaotropic compound or, for example, by employing a lysis buffer containing protein kinase K together with a chaotropic compound.

Particular preference is given according to the invention to lysing the cells by a lysis buffer containing a detergent, an enzyme, a chaotropic compound or a mixture of at least two of these components.

The prior art has disclosed a large number of suitable detergents. Detergents which are particularly preferred according to the invention are selected from the group comprising sodium dodecylsulfate (SDS), polyethylene glycol-phenol ether such as, for example, Triton X-100, Tween, NP-40 or mixtures thereof, with SDS and Triton X-100 being particularly preferred detergents. If the detergent used is SDS, preference is furthermore given according to the invention to using from 1 to 30 mol, preferably 2 to 20 mol and most preferably 3 to 6 mol, NaOH or KOH, particularly preferably NaOH, per mole of SDS for lysis of the cells. If the lysis buffer contains detergents, preference is furthermore given in the method of the invention to lysing the cells in the method step II) in the presence of from 0.01 to 100 μmol, particularly preferably 0.1 to 50 μmol and most preferably 0.25 to 5 μmol of detergent per $10^6$ cells. When using a detergent for lysing the cells, the cells are usually lysed in the presence of a detergent concentration of from 0.005 to 5% (v/v), particularly preferably 0.01 to 1% (v/v) and most preferably 0.025 to 0.5% (v/v), if the detergent is a compound which is liquid at room temperature and atmospheric pressure, or else in the presence of a detergent concentration of from 0.01 to 1% by weight, particularly preferably 0.25 to 5% by weight and most preferably 0.05 to 0.4% by weight, if the detergent is a compound which is solid at room temperature and atmospheric pressure.

Preferred chaotropic compounds are in particular chaotropic salts. A chaotropic salt means for the purpose of the invention preferably a salt which has high affinity for (striving for, attraction to) water and which therefore forms a large tight hydration envelope (shell-like addition of water molecules). Preferred chaotropic salts are in particular guanidinium isothiocyanate or guanidinium hydrochloride, with particular preference being given to guanidinium isothiocyanate. If chaotropic salts are used for lysis of the cells, preference is furthermore given in the method of the invention to the cells being lysed in the method step II) at a chaotropic salt concentration of from 0.5 to 10 mol/l, particularly preferably from 1 to 5 mol/l and most preferably from 2 to 3.5 mol/l. If the lysis buffer contains chaotropic salts, it may optionally also be advantageous for said lysis buffer to contain a water-miscible organic solvent, for example a water-miscible alcohol such as ethanol or isopropanol, in an amount in a range from 10 to 60% by volume, particularly preferably 20 to 50% by volume.

Preferred enzymes are in particular proteases, among which particular preference is given to trypsin, proteinase K, chymotrypsin, papaine, pepsin, pronase and endoproteinase Lys-C and most preference is given to proteinase K. The enzyme concentration in the lysis buffer is preferably in a range from 0.01 to 10% by weight, particularly preferably 0.1 to 5% by weight and most preferably 0.2 to 1% by weight, in each case based on the total weight of the lysis buffer.

The concentration of detergent, chaotropic salt or enzyme in the lysis buffer depends inter alia on the amount of the cells to be lysed and on the manner of the provision of said cells in the method step I). If the cells to be lysed are firstly suspended in a suspension buffer, the lysis buffer contains the detergent, chaotropic salt or enzyme at a concentration which is higher than the concentration of said components which is intended during lysis of the cells. This concentrated lysis buffer is then added to the cell suspension in an amount which is sufficient in order to establish in said cell suspension a chaotropic salt, detergent or enzyme concentration required for lysing the cells as completely as possible and described above. However, if the lysis buffer is applied, for example, directly to adherent cells or contacted with a cell pellet, said lysis buffer contains the detergent, chaotropic salt or enzyme preferably at the concentration which is also present during lysis of the cells.

According to a particular embodiment of the method of the invention, the cells are lysed in the presence of from 0.1 to 1 mol/l, particularly preferably 0.2 to 0.8 mol/l and most preferably 0.3 to 0.7 mol/l, of an alkali metal salt, with preference being given to sodium chloride, potassium chloride and lithium chloride and particular preference being given to sodium chloride. If the cells to be lysed are first suspended in a suspension buffer, then either a suitable amount of the alkali metal salt may be added already to said suspension buffer, or else a lysis buffer is added to the suspension buffer, which contains a correspondingly higher concentration of the alkali metal salt. However, if the lysis buffer is applied, for example, directly to adherent cells or contacted with a cell pellet, then preference is given to said lysis buffer containing the alkali metal salt within the above-described concentration ranges.

A lysis buffer which is particularly suitable according to the invention and which can be added to a cell suspension is a buffer which contains from 1 to 200 mmol/l, particularly preferably 5 to 150 mmol/l and most preferably about 10 to 100 mmol/l NaOH and from 0.01 to 1% (v/v), particularly preferably 0.025 to 0.5% (v/v) and most preferably 0.05 to 0.4% (v/v) SDS and has a pH in a range from 5 to 7, particularly preferably of about 5.5. Preference is given here to adding this lysis buffer to the cell suspension in a volume ratio of preferably from 3:1 to 1:3, particularly preferably from 2:1 to 1:2 and most preferably in a volume ratio of about 1:1.

A lysis buffer which is particularly suitable according to the invention and which can be added to a cell pellet, to adherent cells or to a tissue section or tissue fragment is
- a buffer which contains from 0.1 to 1 mol/l, particularly preferably 0.25 to 0.75 mol/l and most preferably about 0.4 to 0.6 mol/l NaCl and from 0.1 to 10% (v/v), particularly preferably 0.5 to 5% (v/v) and most preferably 0.75 to 1.5% (v/v) Triton X-100 and has a pH within a range from 6 to 8, particularly preferably of about 7, or
- a buffer which contains from 0.5 to 10 mol/l, particularly preferably 1 to 5 mol/l and most preferably about 1.5 to 3 mol/l guanidinium isothiocyanate, from 1 to 50 mmol/l, particularly preferably 5 to 40 mmol/l and most preferably 10 to 20 mmol/l, sodium citrate and from 10 to 60% (v/v), particularly preferably 20 to 50% (v/v) and most preferably 30 to 40% (v/v) ethanol and has a pH within a range from 6 to 8, particularly preferably of about 7, said lysis buffers being added to the cells to be lysed preferably in an amount within a range from 50 to 2000 µl, particularly preferably 100 to 1000 µl and most preferably 150 to 300 µl, per $10^6$ cells.

If the cells represent a tissue section or a tissue fragment, then providing the cells in the method step I) comprises preferably contacting said tissue section or said tissue fragment with liquid nitrogen immediately after removal from a plant or an animal. The tissue section or tissue fragment is then preferably directly contacted with the lysis buffer and, where appropriate, homogenized by means of a suitable homogenizing device.

After the cells have been contacted with the lysis buffer, they are lysed preferably within a temperature range from 15 to 40° C., particularly preferably, however, at room temperature, for a period within a range from 1 to 60 minutes, particularly preferably 2 to 15 minutes.

Before the cell lysate is contacted by way of aqueous phase $P_1$ in the method step ii) with the anion exchange matrix, it may also be advantageous according to a particular embodiment of the method of the invention to separate beforehand one or more of the components ($\alpha 2$) different from the nucleic acid ($\alpha 1$) from the cell lysate. In principle, any separating methods known to the skilled worker, such as for example precipitation reactions, separation by dialysis or chromatography or else an extraction, may be employed for said separation, with particular preference being given to an extraction, in particular an extraction with acidic phenol or mixtures of phenol and chloroform and most preference being given to an extraction with acidic phenol. This involves contacting and thoroughly mixing, for example using a vortex, the acidic phenol with the cell lysate, preferably in a volume ratio within a range from 3:1 to 1:3, particularly preferably from 2:1 to 1:2 and most preferably in a volume ratio of about 1:1. The composition is then centrifuged and the aqueous phase is separated from the organic phase. In this way, one or more components different from the nucleic acid ($\alpha 1$) have been diluted in the separated aqueous phase which is then subjected as phase $P_1$ to the method step ii).

In the method step ii) of the method of the invention the aqueous phase $P_1$ is then contacted with an anion exchange matrix in order to attach the nucleic acid ($\alpha 1$) to said anion exchange matrix.

It is possible here in principle to use as anion exchange matrix any materials having functional groups which are at least partially in the cationic form under the conditions under which the aqueous phase $P_1$ is contacted with the anion exchange matrix, in particular under the pH conditions.

The anion exchange matrix is preferably a solid comprising an electrically neutral matrix. This matrix is defined by the size, form, porosity, mechanical properties and the positively charged functional groups preferably bound covalently to the solid scaffolding. The three most common classes of matrix materials are orthosilicic acid, polysaccharides and synthetic polyolefins, with the polyolefins applied being mainly polystyrene or poly(meth)acrylic resins. Poly(meth)acrylic resins include polymers of numerous substituted (meth)acrylic amides (=poly(meth)acryl amides) and (meth)acrylic esters (=poly(meth)acrylates), it being possible for the (meth)acrylic acid monomer to bear alkyl substituents on the C-2 or the C-3 atom. Particularly preferred functional groups bound to the matrix are functional groups selected from the group comprising primary, secondary or tertiary amino groups, phosphine groups, hydrazine groups and imine groups. Most preference is given to the anion exchange matrix being scaffolding materials to which diethylaminoethyl groups (DEAE, $[CH_3CH_2)_2N—CH_2—CH_2—]_a$) are covalently bound, in particular DEAE cellulose, and linear or branched polyethylenimines comprising $[—CH_2—CH_2—NH—]$ groups and/or $[—CH_2—CH_2—N(CH_2CH_2—NH_2)—]$ groups. The anion exchange matrix may furthermore be employed by way of filler material, for example in a separating column. However, coating of other materials, in particular particles, filters, membranes, monoliths or other organic or inorganic surfaces such as microtiter plates, which do not consist of a material with anion exchange properties, or of other reaction vessels with the anion exchange matrix is also conceivable.

Particular preference is given here according to the invention to the anion exchange matrix being in the form of a coating on magnetic or nonmagnetic, very particularly preferably, however, on magnetic, most preferably on superparamagnetic, ferrimagnetic or ferromagnetic, particles. Compared with nonmagnetic particles, magnetic particles have the advantage of forming magnetic aggregates, enabling them to be removed gently, rapidly and efficiently from the aqueous phase $P_1$.

Preferred magnetic particles which can be coated with the anion exchange matrix are available, for example, from Dynal, Advanced Magnetics Inc., Biotechnologies Ltd., Amersham, Promega, Scigen, Advanced Genetic Technologies and Seradyn. Suitable magnetic particles are in particular those described in WO-A-83/03920 and the particles sold as DYNA-BEADS by Dynal AS (Oslo, Norway). If the anion exchange matrix employed is polyethyleneimines, particular preference is given to epoxide-functionalized magnetic particles, for example those available under the name "M-PVA E0x" from Chemagen AG, Baesweiler, Germany. Also conceivable is the use of carboxylate-functionalized particles which can likewise be obtained from Chemagen AG under the product names "M-PVA C11" or "M-PVA C12". The magnetic particles have an average diameter within a range from preferably 0.1 to 100 µm, particularly preferably 0.5 to 50 µm and most preferably 1 to 10 µm, while the specific surface is within a range of preferably 0.5 to 250 $m^2/g$, particularly preferably within a range from 1 to 50 $m^2/g$.

According to a specific embodiment of the method of the invention, preference is given according to the invention to attaching the nucleic acids ($\alpha 1$) to the anion exchange matrix in the method step ii) at a pH preferably within a range from 2 to 10, particularly preferably within a range from 3 to 7 and most preferably within a range from 4 to 6.

If the aqueous phase $P_1$ used in the method step ii) has a pH which is different from these pH values, which may be the case in particular when using an alkaline, SDS-containing lysis buffer, it may be necessary to adjust the pH in the aqueous phase, for example by adding a neutralization buffer, to the desired value prior to or during contacting the aqueous phase $P_1$ with the anion exchange matrix. Said neutralization buffer comprises preferably an alkali metal salt of acetic acid, particularly preferably potassium acetate, at a concentration within a range from 10 to 10000 mmol/l, particularly preferably within a range from 50 to 5000 mmol/l and most preferably within a range from 100 to 1000 mmol/l, the neutralization solution having a pH preferably within a range from 2 to 8, particularly preferably within a range from 4 to 6. The pH in the solution of the alkali metal salt of acetic acid is adjusted to a value within the above-described ranges preferably by adding acetic acid.

According to a specific embodiment of the method of the invention, preference may furthermore be given to the nucleic acid ($\alpha$1) being attached to the anion exchange matrix in the method step ii) in the presence of an alkali metal salt, preferably in the presence of potassium chloride, sodium chloride or lithium chloride, particularly preferably however in the presence of sodium chloride, the concentration of said alkali metal salts during attachment being preferably within a range from 0.01 to 10 mol/l, particularly preferably within a range from 0.05 to 5 mol/l and most preferably within a range from 0.25 to 0.75 mol/l. These salt concentrations may be adjusted during attachment by adding an appropriately concentrated salt solution to the initially introduced aqueous phase $P_1$, for example a cell lysate, or else by suspending cells in the presence of a suspension buffer or lysing said cells in the presence of a lysis buffer, either of which buffer has an appropriate salt concentration.

According to another, specific embodiment of the method of the invention, preference may furthermore be given to the nucleic acid ($\alpha$1) being attached to the anion exchange matrix in the method step ii) in the presence of a chaotropic substance, in particular a chaotropic salt such as guanidinium isothiocyanate, the concentration of said chaotropic salts during attachment being preferably within a range from 0.1 to 10 mol/l, particularly preferably within a range from 0.5 to 5 mol/l and most preferably within a range from 1 to 3 mol/l. In this specific embodiment of the method of the invention it may furthermore also be advantageous to carry out attachment in the presence of water-miscible, organic solvents, in particular in the presence of alcohols such as ethanol or isopropanol at a concentration within a range from 10 to 70% by volume, particularly preferably 20 to 60% by volume.

The nucleic acid ($\alpha$1) may be attached to the anion exchange matrix in the method step ii) preferably by passing, when using the anion exchange matrix as filler material in a column, the aqueous phase $P_1$, for example the cell lysate which meets the above-described advantageous pH conditions and which contains the above-described salts at the specified concentrations, over the column material, preferably at temperatures within a range from 1 to 30° C., particularly preferably 2 to 25° C., for example at room temperature. The aqueous phase $P_1$ may be passed through the column material, where appropriate, by means of overpressure, vacuum, centrifugation or support by means of capillary forces.

When using anion exchange matrix-coated particles, attachment is preferably carried out by continuously agitating the aqueous phase $P_1$ contacted with the particles, for example by means of a shaker, said attachment in this case also being carried out preferably at temperatures within a range from 1 to 30° C., particularly preferably 2 to 25° C., for example at room temperature.

After the nucleic acids ($\alpha$1) have been attached to the anion exchange matrix, the latter may optionally be washed by means of a washing buffer in a method step iii). If the anion exchange matrix has been used as filler material in a column, washing is preferably carried out by passing the washing buffer over the column, it being possible also here to utilize overpressure, a vacuum, centrifugation or capillary forces. If, for example, anion exchange matrix-coated nonmagnetic particles have been used, then said particles are first removed from the aqueous phase $P_1$, for example by means of filtration or centrifugation, and then washed with the washing buffer. When using anion exchange matrix-coated magnetic particles, washing is carried out preferably by exposing the reaction vessel which contains the magnetic particles contacted with the aqueous phase $P_1$ to a magnet, causing said magnetic particles to adhere to the inner walls of the reaction vessel due to the magnetic field. Under these circumstances, the aqueous phase $P_1$ may readily be removed and replaced with the washing buffer. Devices suitable for this are available, for example, from Dynal, Oslo, Norway.

The washing buffer may be, for example, RNase-free water, mixtures of water and water-soluble organic solvents, such as mixtures of water with from 1 to 80% by volume of a water-soluble alcohol, for example with from 1 to 80% by volume ethanol or isopropanol, or aqueous salt solutions, in particular aqueous acetate solutions, for example aqueous sodium acetate solution with a sodium acetate concentration within a range from 1 to 50 mmol/l, particularly preferably 5 to 25 mmol/l, with particular preference being given to the pH of said washing buffer being within a range from 4 to 9.

The washing step may be repeated as required once, twice, three times, where appropriate even more often, using in each case a fresh washing buffer.

After the nucleic acid ($\alpha$1) has been attached to the anion exchange matrix in the method step ii) and optional washing in the method step iii), the nucleic acid ($\alpha$1) bound to the anion exchange matrix is removed from the anion exchange matrix in the method step iv), resulting in a fluid, preferably aqueous, phase $P_2$ containing the nucleic acid ($\alpha$1).

Said removal is preferably carried out by way of elution by contacting the anion exchange matrix with an elution buffer which dissolves binding between the functional groups of the anion exchange matrix and the nucleic acid ($\alpha$1), resulting in an eluate as fluid phase $P_2$ which contains the nucleic acid ($\alpha$1).

If the anion exchange matrix has been used as filler material in a column, the elution is preferably carried out by passing the elution buffer over the column, it being possible again to utilize an overpressure, a vacuum, a centrifugation or capillary forces. If, for example, anion exchange matrix-coated, nonmagnetic particles have been used, then these particles are first removed from the aqueous phase $P_2$ or from the washing buffer, for example by means of filtration or centrifugation, and then contacted with the elution buffer. When using anion exchange matrix-coated magnetic particles, elution is preferably carried out by exposing the reaction vessel which contains the magnetic particles contacted with the aqueous phase $P_1$ or the washing buffer to a magnet, causing said magnetic particles to adhere to the inner walls of the reaction vessel due to the magnetic field. Under these circumstances, the aqueous phase $P_1$ or else the washing buffer may readily be removed and replaced with the elution buffer.

The elution buffer is preferably an aqueous salt solution, in particular aqueous solutions containing alkali metal halides such as NaCl, KCl or LiCl, alkaline earth halides such as $CaCl_2$ or $MgCl_2$, ammonium salts such as ammonium chloride or ammonium sulfate or mixtures of at least two of these salts, it also being possible for the elution buffer to optionally contain buffer systems such as alkali metal acetate/acetic acid or buffer systems based on tris(hydroxymethyl)aminomethane.

According to a specific embodiment of the method of the invention, the elution buffer contains water-soluble calcium salts such as $CaCl_2$, water-soluble magnesium salts such as $MgCl_2$, water-soluble ammonium salts such as ammonium sulfate or ammonium chloride or mixtures of at least two of these salts. If the elution buffer contains $CaCl_2$, then this salt is preferably at a concentration within a range from 1 to 1000 mmol/l, particularly preferably from 5 to 500 mmol/l and most preferably 10 to 100 mmol/l. If the elution buffer contains $MgCl_2$, then this salt is preferably at a concentration within a range from 1 to 1000 mmol/l, particularly preferably 5 to 500 mmol/l and most preferably 10 to 100 mmol/l. If the elution buffer contains ammonium sulfate and/or ammonium chloride, then these salts are preferably at a total concentration within a range from 1 to 1000 mmol/l, particularly preferably 5 to 500 mmol/l and most preferably 20 to 300 mmol/l. The pH of the elution buffer is preferably within a range from 5 to 12, preferably 6 to 10, and particularly preferably 7 to 10.

Especially elution buffers which contain preferably exclusively calcium salts, in particular $CaCl_2$, and/or ammonium salts, preferably ammonium sulfate and/or ammonium chloride, as salts are particularly suitable for enriching selectively miRNA over tRNA. Thus it is possible to achieve good enrichment of miRNA with simultaneous dilution of tRNA by using elution buffers consisting of water and $CaCl_2$ at a concentration of preferably up to 60 mmol/l and also by using elution buffers consisting of water and ammonium sulfate or ammonium chloride at a concentration of preferably up to 170 to 200 mmol/l, and these elution buffers are therefore particularly suitable for selective enrichment of miRNA from miRNA- and tRNA-containing compositions.

Elution buffers which are particularly suitable according to the invention are an elution buffer $EP_1$ which contains from 1 to 10 000 mmol/l, particularly preferably 10 to 5000 mmol/l and most preferably 50 to 1000 mmol/l TRIS, from 1 to 1000 mmol/l, preferably 5 to 800 mmol/l and most preferably 10 to 500 mmol/l, of an alkali metal salt, preferably NaCl or KCl, from 1 to 400 mmol/l, particularly preferably 10 to 300 mmol/l and most preferably 50 to 200 mmol/l, of an ammonium salt, preferably ammonium sulfate or ammonium chloride, and from 0.1 to 200 mmol/l, particularly preferably 0.5 to 100 mmol/l and most preferably 1 to 50 mmol/l, of a magnesium salt, preferably magnesium chloride, dissolved in water, and which has a pH preferably within a range from 7 to 11, particularly preferably 8 to 10;

an elution buffer $EP_2$ which contains from 1 to 1000 mmol/l, particularly preferably 5 to 500 mmol/l and most preferably 10 to 100 mmol/l, of a magnesium salt, preferably magnesium chloride, dissolved in water, and which has a pH preferably within a range from 6 to 10, particularly preferably 7 to 9;

an elution buffer $EP_3$ which contains from 1 to 1000 mmol/l, particularly preferably 5 to 500 mmol/l and most preferably 10 to 100 mmol/l, of a calcium salt, preferably calcium chloride, dissolved in water, and which has a pH preferably within a range from 6 to 10, particularly preferably 7 to 9;

an elution buffer $EP_4$ which contains from 1 to 1000 mmol/l, particularly preferably 5 to 500 mmol/l and most preferably 20 to 300 mmol/l, of an ammonium salt, preferably ammonium chloride or ammonium sulfate, dissolved in water, and which has a pH preferably within a range from 6 to 10, particularly preferably 7 to 9;

an elution buffer $EP_5$ which contains from 1 to 2000 mmol/l, particularly preferably 10 to 1000 mmol/l and most preferably 100 to 500 mmol/l, of an alkali metal salt, preferably potassium chloride, sodium chloride or lithium chloride, dissolved in water, and which has a pH preferably within a range from 6 to 10, particularly preferably 7 to 9.

More specifically, the elution buffers $EP_1$ to $EP_4$ are suitable for purifying miRNA from compositions containing miRNA and tRNA, while the elution buffer $EP_5$ is particularly suitable for generally purifying nucleic acids with a length of less than 300 nucleotides, in particular less than 100 nucleotides, from compositions which contain aside from said nucleotides also longer-chain nucleic acids. It is moreover possible to regulate selectively the enrichment of miRNA over tRNA from compositions containing miRNA and tRNA by means of increasing concentrations of $Mg^{2+}$, $Ca^{2+}$ and $NH_4^+$ in the elution buffers $EP_2$ to $EP_4$.

According to a particular embodiment of the method of the invention, preference is given to the relative amount of RNA with a length of less than 300 nucleotides, preferably less than 100 nucleotides and most preferably less than 25 nucleotides, in the aqueous phase $P_2$, based on the total amount of RNA in the aqueous phase $P_2$, being greater by a factor of at least 2, particularly preferably at least 4, additionally preferably at least 6, additionally even more preferably at least 10 and most preferably at least 20, than the relative amount of RNA with a length of less than 300 nucleotides, preferably less than 100 nucleotides and most preferably less than 25 nucleotides, in the aqueous phase $P_1$, based on the total amount of RNA in the aqueous phase $P_1$.

In a further specific embodiment of the method of the invention, in particular in the embodiment which employs any of the elution buffers $EP_1$ to $EP_4$, preference is given to the relative amount of miRNA in the aqueous phase $P_2$, based on the total amount of miRNA and tRNA in the aqueous phase $P_2$, being greater by a factor of at least 2, particularly preferably at least 4, additionally preferably at least 6, additionally even more preferably at least 10 and most preferably at least 20, than the relative amount of miRNA in the aqueous phase $P_1$, based on the total amount of miRNA and tRNA in the aqueous phase $P_1$.

A contribution to the solution of the objects mentioned at the outset is also made by a kit for enriching nucleic acids with a length of less than 300 nucleotides, preferably less than 100 nucleotides and most preferably less than 25 nucleotides, comprising:

(β1) a lysis buffer or a lysis buffer concentrate,
(β2) an anion exchange matrix,
(β3) an elution buffer,
(β4) optionally a suspension buffer,
(β5) optionally a neutralization buffer,
(β6) optionally a washing buffer, and
(β7) optionally an extractant, for example phenol, an alcohol such as, for example, ethanol or mixtures thereof.

Such a kit may be used for carrying out the above-described method.

Preferred suspension buffers (β4), lysis buffers (β1), neutralization buffers (β5), washing buffers (β6) and elution buffers (β3) are those buffers which have already been mentioned as preferred buffers in connection with the method of the invention. The lysis buffer concentrate is a buffer which contains the compound effective for lysis, in particular the detergent or the chaotropic salt, at a concentration which is higher than the concentration during lysis of the cells. A lysis buffer concentrate of this kind is used in particular, if cell suspensions are intended to be used as starting material from which the short-chain nucleic acids are to be isolated, in which cell suspensions the lysis conditions required for lysis may then be adjusted by adding defined amounts of said lysis buffer concentrate.

Suitable as anion exchange matrix (β2) are likewise materials which have been mentioned above as preferred anion exchange matrix in connection with the method of the invention for enriching nucleic acids, for example in particular also magnetic or nonmagnetic particles coated with an anion exchange matrix.

According to a particular embodiment of the kit of the invention, said kit includes as anion exchange matrix (β2) magnetic particles coated with an anion exchange matrix and as elution buffer (β3) any of the buffers selected from the group comprising $EP_1$, $EP_2$, $EP_3$ and $EP_4$.

A contribution to the solution of the objects mentioned at the outset is furthermore made by the use of the above-described kit in the method of the invention described at the outset for purifying nucleic acids with a length of less than 300 nucleotides, preferably less than 200 nucleotides, particularly preferably less than 100 nucleotides, additionally preferably less than 50 nucleotides and most preferably less than 25 nucleotides.

A contribution to the solution of the objects mentioned at the outset is also made by the use of an anion exchange matrix for purifying nucleic acids with a length of less than 300 nucleotides, preferably less than 200 nucleotides, particularly preferably less than 100 nucleotides, additionally preferably less than 50 nucleotides and most preferably less than 25 nucleotides, wherein preference is given to said anion exchange matrix and said nucleotides being those compounds which have been mentioned above at the outset as preferred components in connection with the method of the invention for purifying nucleic acids.

Finally, a contribution to the solution of the objects mentioned at the outset is also made by a method for treating a disease, comprising the method steps of:
(γ1) diagnosing the disease by a diagnostic method which comprises enriching nucleic acids with a length of less than 300 nucleotides, preferably less than 200 nucleotides, particularly preferably less than 100 nucleotides, additionally preferably less than 50 nucleotides and most preferably less than 25 nucleotides, according to the purification method described at the outset, and
(γ2) therapeutically treating the disease diagnosed.

The disease to be treated may be any diseases whose cause or progress correlates in any way with the kind and amount of the nucleic acids present in particular body cells or bodily fluids, which nucleic acids have a length of less than 300 nucleotides, preferably less than 200 nucleotides, particularly preferably less than 100 nucleotides, additionally preferably less than 50 nucleotides and most preferably less than 25 nucleotides, in particular, however, with the kind and amount of miRNA, whether a change in the kind and amount of these nucleic acids, in comparison with a healthy patient, is the cause of the disease or whether a change in the kind and amount of these nucleic acids, in comparison with a healthy patient, is a consequence of said disease.

The invention will be illustrated in more detail on the basis of non-limiting figures and examples.

FIG. 3 depicts a silver nitrate-stained, 15% strength polyacrylamide gel which was used for fractionating the eluate obtained in Example 3 (duplicate application in the gel).

FIG. 4 depicts a silver nitrate-stained, 15% strength polyacrylamide gel which was used for fractionating the eluate obtained in Example 4 (duplicate application in the gel).

FIG. 5 depicts a silver nitrate-stained, 15% strength polyacrylamide gel which was used for fractionating the eluate obtained in Example 5 (duplicate application in the gel).

EXAMPLES

In the following examples, miRNAs were spiked into a cellular background.

Example 1

$10^6$ Jurkat cells were mixed with 1 μg of miR177 antisense miRNA and lysed with the aid of 550 μl of a lysis buffer containing 0.5 M NaCl, 1% (v/v) Triton X-100. After incubating on ice for 10 minutes, 550 μl of acidic phenol were added. Vortexing was followed by centrifugation at 20 800×g for 5 minutes, the aqueous phase was removed and mixed with 652 μg of magnetic particles coated with polyethylenimine.

The particles were obtained by suspending 4 g of epoxide-functionalized magnetic particles (M-PVA E0x particles from Chemagen AG, Baesweiler, Germany) in 50 ml of a 10% strength high molecular weight polyethyleneimine solution (Sigma-Aldrich, Aldrich Cat No. 40,872-7) in water, pH 10, transferred to a round bottom flask and heated to 60° C. with stirring for 10 hours. This mixture was then washed six times with desalted water with magnetic removal.

Figure 1:
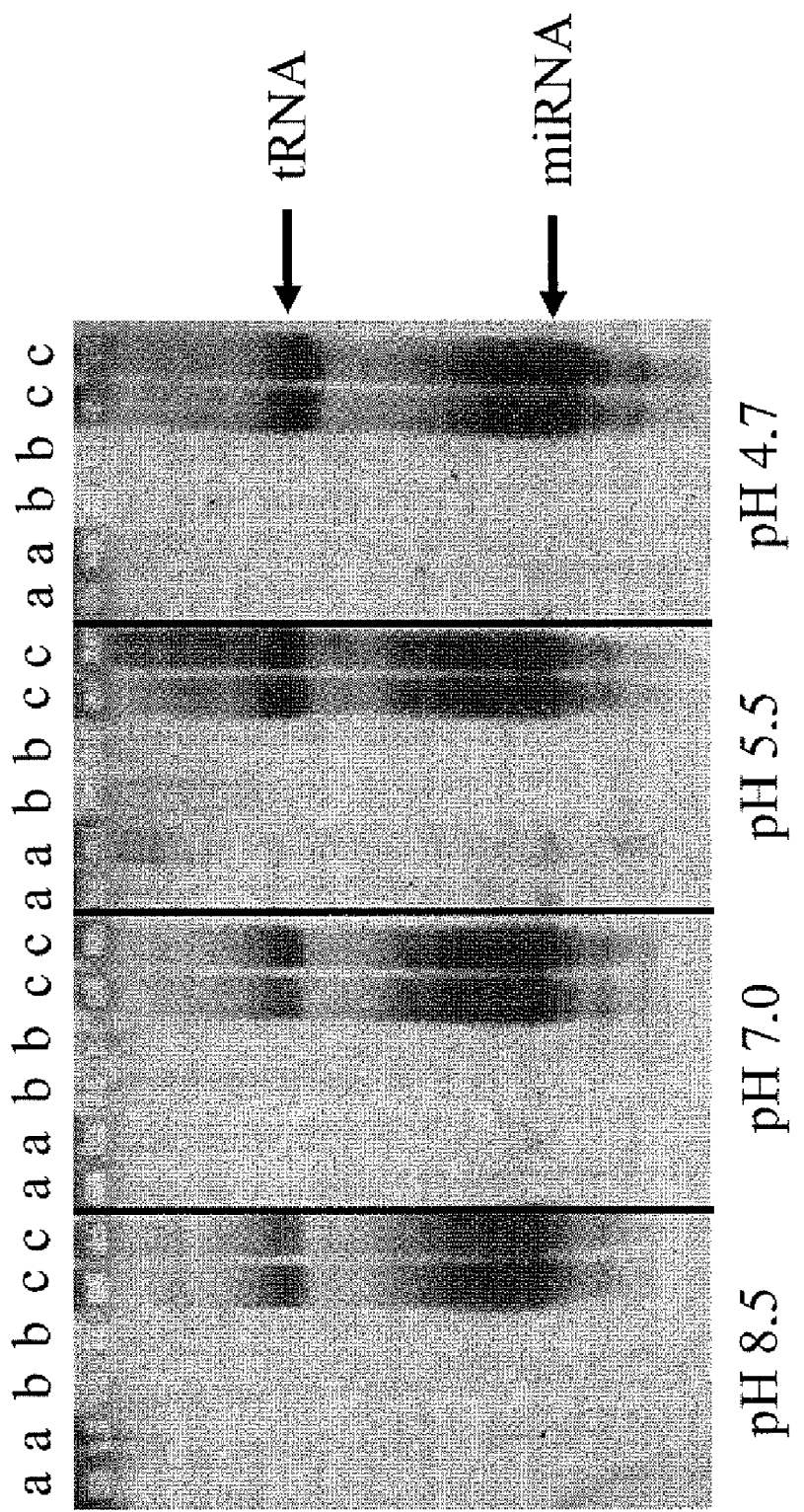
FIG. 1 depicts a silver nitrate-stained, 15% strength polyacrylamide gel which was used for fractionating the eluates obtained in Example 1 (duplicate application in the gel; a=washing buffer after first washing, b=washing buffer after second washing, c=eluate).

After shaking on a plate shaker for 5 minutes, the supernatant was discarded followed by washing twice with 500 μl of water adjusted to pH 4.7, 5.5, 7.0 or 8.5 (lanes a and b in the gel of FIG. 1). Elution was carried out with 20 μl of a buffer containing 1 mol/l Tris/Cl, pH 9.5, 400 mmol/l KCl, 100 mmol/l ammonium sulfate and 30 mmol/l $MgCl_2$. Aliquots of the eluates were applied to a 15% polyacrylamide gel and stained with silver nitrate (lanes c in FIG. 1).

Using 0.5 mol/l NaCl as lysis buffer, it is possible to efficiently purify miRNAs, with only miRNAs and tRNAs still remaining in the eluates upon elution and all other nucleic acid species having been diluted by the purification procedure.

Example 2

Figure 2:
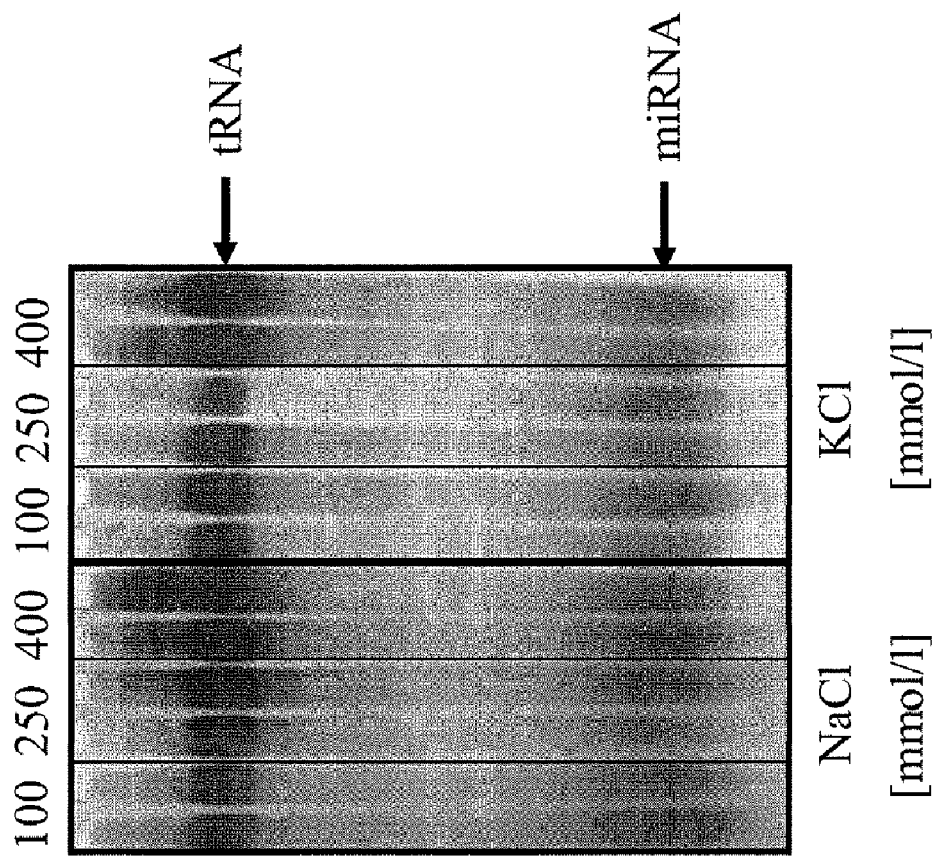
FIG. 2 depicts a silver nitrate-stained, 15% strength polyacrylamide gel which was used for fractionating the eluates obtained in Example 2 (duplicate application in the gel).

$10^6$ Jurkat cells were mixed with 1 μg of let7a antisense RNA, lysed and bound to magnetic particles, as specified in Example 1. After two washing steps with water, elution was carried out with 20 μl of buffer, 100 mmol/l NaCl, 250 mmol/l NaCl, 400 mmol/l NaCl, 100 mmol/l KCl, 250 mmol/l KCl and 400 mmol/l KCl being used as elution buffer. Aliquots of the eluates were applied to a 15% polyacrylamide gel and stained with silver nitrate (FIG. 2).

This experiment reveals that salts at different molarities are suitable for elution. When using NaCl, KCl and LiCl (data not shown) as elution buffer, both tRNAs and miRNAs can be purified in high quantities.

Example 3

The procedure was as in Example 2, using buffers containing from 10 to 100 mmol/l $MgCl_2$ as elution buffers. Aliquots of the eluates were applied to a 15% polyacrylamide gel and stained with silver nitrate (FIG. 3).

This experiment demonstrates that miRNAs can also be purified with the aid of $MgCl_2$ as elution buffer. If low molarities of $MgCl_2$ are used as elution buffer, the tRNAs and longer nucleic acids are comparatively diluted, while the miRNAs can be recovered with very good yields.

Example 4

The procedure was as in Example 2, using buffers containing from 10 to 85 mmol/l $CaCl_2$ as elution buffers. Aliquots of the eluates were applied to a 15% polyacrylamide gel and stained with silver nitrate (FIG. 4).

Up to a $CaCl_2$ molarity of about 50 mmol/l, miRNAs can be eluted with a very good rate of recovery, while the eluates contain only traces of tRNAs. If the molarity is increased further, it is additionally also possible to eluate tRNAs with a good rate of recovery.

Example 5

The procedure was as in Example 2, using buffers containing from 25 to 400 mmol/l ammonium sulfate or from 25 to 400 mmol/l ammonium chloride as elution buffers. Aliquots of the eluates were applied to a 15% polyacrylamide gel and stained with silver nitrate (FIG. 5).

Especially ammonium salts, together with calcium chloride, exhibit the best properties during elution in order to achieve a high yield of miRNA with a simultaneously very low yield of tRNA. Up to an ammonium salt concentration in the eluate of up to about 170 to 200 mmol/l, the yield of tRNA remains relatively low, while the yield of miRNA at these molarities is very good. From a concentration of about 400 mmol/l upwards, very large quantities of tRNA can also be found in the eluates.

The invention claimed is:

1. A method for enriching at least one nucleic acid with a length of not more than 300 nucleotides relative to at least one least one nucleic acid with a length of more than 300 nucleotides, comprising
    i) providing a fluid phase $P_1$ comprising
        ($\alpha 1$) said at least one nucleic acid with a length of not more than 300 nucleotides, and
        ($\alpha 2$) said at least one nucleic acid with a length of more than 300 nucleotides,
    ii) contacting the phase $P_1$ with an anion exchange matrix to bind the nucleic acid ($\alpha 1$) to the anion exchange matrix, wherein the anion exchange matrix comprises a functional group selected from the group consisting of amino groups, phosphine groups, hydrazine groups and imine groups;
    iii) optionally washing the anion exchange matrix with a washing buffer, wherein the nucleic acid ($\alpha 1$) remains bound to the anion exchange matrix, and
    iv) eluting the nucleic acid ($\alpha 1$) bound to the anion exchange matrix from said anion exchange matrix by a method comprising contacting said anion exchange matrix with an aqueous elution buffer comprising a uniform concentration of a salt to obtain a fluid phase $P_2$ comprising the nucleic acid ($\alpha 1$), wherein the elution buffer comprises a salt selected from the group consisting of: a water-soluble calcium salt, a water-soluble magnesium salt, a water-soluble ammonium salt, and mixtures thereof.

2. The method as claimed in claim 1, wherein the nucleic acid ($\alpha 1$) is an RNA.

3. The method as claimed in claim 2, wherein the RNA is at least one selected from the group consisting of miRNA, pre-miRNA, siRNA, snRNA, snoRNA, tRNA, 5S-rRNA and 5.8S-rRNA.

4. The method as claimed in claim 3, wherein the RNA is miRNA, pre-miRNA, tRNA and/or a mixture of miRNA and tRNA.

5. The method as claimed in claim 1, wherein the anion exchange matrix is present in the form of a coating on a particle, a filter, a membrane, a monolith, a microtiter plate and/or other reaction vessels.

6. The method as claimed in claim 5, wherein the particle is a magnetic particle.

7. The method as claimed in claim 1, wherein the nucleic acid ($\alpha 1$) is bound to the anion exchange matrix in the method step ii) in the presence of from 0.01 to 10 mol/l NaCl.

8. The method as claimed in claim 1, wherein the washing buffer is RNase-free water.

9. The method as claimed in claim 1, wherein the elution buffer comprises calcium chloride at a concentration in a range from 1 to 1000 mmol/l.

10. The method as claimed in claim 1, wherein the elution buffer comprises magnesium chloride at a concentration in a range from 1 to 1000 mmol/l.

11. The method as claimed in claim 1, wherein the elution buffer comprises ammonium sulfate or ammonium chloride at a concentration in a range from 1 to 1000 mmol/l.

12. The method as claimed in claim 1, wherein the aqueous phase $P_1$ provided in the method step i) is a cell lysate.

13. The method as claimed in claim 12, wherein the cell lysate is obtainable by a method comprising the method steps of
    I) providing cells,
    II) lysis of the cells to obtain a cell lysate, and
    III) optionally separating at least partially the at least one component ($\alpha 2$) different from the nucleic acid ($\alpha 1$) from the cell lysate.

14. The method as claimed in claim 2, wherein the relative amount of RNA with a length of not more than 300 nucleotides in the phase $P_2$, based on the total amount of RNA in the phase $P_2$, is greater by a factor of at least 2 than the relative amount of RNA with a length of not more than 300 nucleotides in the phase $P_1$, based on the total amount of RNA in the phase $P_1$.

15. The method as claimed in claim 4, wherein the relative amount of miRNA in the aqueous phase $P_2$, based on the total amount of miRNA and tRNA in the aqueous phase $P_2$, is greater by a factor of at least 2 than the relative amount of miRNA in the aqueous phase $P_1$, based on the total amount of miRNA and tRNA in the aqueous phase $P_1$.

16. The method of claim 1 wherein the nucleic acid ($\alpha 1$) is 25 nucleotides or less in length.

17. The method of claim 1 wherein elution is performed with a single aqueous elution buffer.

* * * * *